United States Patent [19]
Blaser et al.

[11] Patent Number: 5,470,958
[45] Date of Patent: Nov. 28, 1995

[54] **ANTISERA AGAINST A PEB1 ANTIGEN FROM *CAMPYLOBACTER JEJUNI***

[75] Inventors: Martin J. Blaser, Nashville, Tenn.; Richard T. Ellison, III, Denver, Colo.; Zhi H. Pei, Nashville, Tenn.

[73] Assignee: Enteric Research Laboratories Inc., Nashville, Tenn.

[21] Appl. No.: 307,480

[22] Filed: Sep. 16, 1994

Related U.S. Application Data

[60] Continuation of Ser. No. 986,928, Dec. 8, 1992, abandoned, which is a division of Ser. No. 612,330, Nov. 13, 1990, Pat. No. 5,200,344.

[51] Int. Cl.$^6$ .................. A61K 35/16; A61K 39/106
[52] U.S. Cl. .................. 530/389.5; 424/164.1; 435/252.1; 435/7.32; 435/822
[58] Field of Search ............... 424/164.1; 435/252.1, 435/7.32, 822; 530/389.5

[56] References Cited

U.S. PATENT DOCUMENTS

| | | | |
|---|---|---|---|
| 4,404,194 | 9/1983 | Arala-Chaves | 514/2 |
| 4,683,195 | 7/1987 | Mullis et al. | 435/6 |
| 4,704,362 | 11/1987 | Itakura et al. | 435/252.3 |
| 4,785,086 | 11/1988 | Rashtchian et al. | 536/24.32 |
| 4,800,159 | 1/1989 | Mullis et al. | 435/91.2 |
| 4,879,213 | 11/1989 | Fox et al. | 435/5 |
| 4,882,271 | 11/1989 | Evans et al. | 435/7.32 |
| 4,965,188 | 10/1990 | Mullis et al. | 435/6 |
| 5,200,344 | 4/1983 | Blaser et al. | 435/7.32 |

FOREIGN PATENT DOCUMENTS

90/14837  12/1990  WIPO.
92/08485  5/1992  WIPO.

OTHER PUBLICATIONS

Blaser et al, Human Serum Antibody Response to *Camphylobacter jejuni* Infection as Measured in an Enzyme–Linked Immunosorbent Assay, Infection and Immunity 44(2):292–298, 1984.
Ramaniuk, et al., *FEMS Microbiology Letters* 43:331–335 (1987).
Fauchere, et al., *Res. Microbiol.* 140:379–382 (1989).
Lee, et al., *Science* 239:1288–1291 (1988).
Bowie, et al., *Science* 247:1306–1310 (1990).
Kumar, et al., *PNAS* 87:1337–1341 (1990).
Young, *PNAS* 80:1194–1198 (1983).
Pennock, et al., *Mol. Cell. Bio.* 4(3):399–406 (1984).
Blaser, et al., *Infection and Immunity* (1983) 42(1) pp. 276–284.
Blaser, et al., *Infection and Immunity* (1986) 53(1) pp. 47–52.
Meinersmann, et al., *Current Microbiology* (1990) 21(1) pp. 17–21.
De Melo, et al., *Infection and Immunity* (1990) 58(6) pp. 1749–1756.
Pei, et al., *J. Bio. Chem.* (1991) 266(25) pp. 16363–16369.
Black, et al., *Dev. Biol. Stand* (1983) 53:9–14.
Brake, et al., *Proc. Nat'l Acad. Sci.* 81(15):4642–6 1984.
Tizard, *An Introduction to Veterinary Immunology*, pp. 178–182 (1982).
Ferrero, et al., *J. Bacteriol.* 174:4212 (1992).
Kervella, et al., *Infection and Immunity* 61(8):3440–3448 (1993).

(List continued on next page.)

Primary Examiner—Hazel F. Sidberry
Assistant Examiner—Julie Krsek-Staples
Attorney, Agent, or Firm—Ostrolenk, Faber, Gerb & Soffen

[57] ABSTRACT

An antigenic composition includes antigens obtainable from *Campylobacter jejuni* and may be used as a vaccine to induce protective antibodies against both *Campylobacter coli* and *Campylobacter jejuni*. The antigenic composition, and antisera specific to the antigens can be used to detect *Campylobacter coli* or *Campylobacter jejuni* infection. Diagnostic detection kits include the novel antigenic composition or antisera thereto.

1 Claim, 6 Drawing Sheets

OTHER PUBLICATIONS

Blaser, et al., *N. Eng. J. Med.* (1981) 305:1444–1452.
Blaser, et al., *Ann. Intern. Med.* (1983) 98:360–365.
Glass, et al., *J. Infect. Dis.* (1983) 148:292–296.
Blaser, et al., *Epidemiologic Reviews* (1983) 5:157–176.
Blaser, et al., *Infect. Immun.* (1984) 44:292–298.
Black, et al., *J. Infect. Dis.* (1988) 157:472–479.
Perlman, et al., "Humoral Immune Response to *Campylobacter jejuni* in Human Volunteers" Abst./87th Ann. Meet. Amer. Soc. for Microbio. (Mar. 1987).
Perlman, et al., "Immunity to *Campylobacter jejuni* Following Oral Challenge to Volunteers" Abst./4th Int'l Wkshp on Campylobacter Infec. (Jun. 1987).
Blaser, et al., *JAMA* (1987) 257:43–46.
Pei, et al., *J. Biol. Chem.* (1988) 263:6416–6420.
Miotti, *Eur. J. Epidemiol.* (1987) 3:356–364.
Blaser, et al., *Infection and Immunity* (1984) vol. 43, No. 3, pp. 986–993.
Dunn, et al., *Infection and Immunity,* vol. 55, No. 7, pp. 1564–1572 (Jul. 1987).
Ames; G. F. L., *J. Biol. Chem.* (1974) 249:634–644.
Oakley, et al., *Anal. Biochem.* (1980) 105:361–363.
Pei, et al., *J. Clin. Invest.* (1990) 85:1036–1043.
Markwell, et al., *Anal. Biochem.* (1978) 87:206–210.
Willoughby, et al., *Anal. Biochem.* (1983) 130:353–358.
Jones, B. N., *J. Liq. Chromatogr.* (1981) 4:565–568.
Towbin, et al., *Proc. Nat'l. Acad. Sci.* (1979) 76:4350–54.
Burnette, et al., *Biochem.* (1981) 112:195–203.
Eldridge, et al., *Curr. Top. Microbiol. Immunol.* (1989) 146:59.
Klugman, et al., *The Lancet,* Nov. 21, 1987, pp. 1165–1169.
Dubreuil, et al., *J. Clin. Microbiol.* (1990) 28(6):1321–1328.
Arnon, *Synthetic Vaccines I:L* 83–92, CRC Press, Inc.
Birnboim and Doly, *Nucleic Acids. Res.,* 7:1513–1523 (1979).
Carbonell, et al., *J. Virol.,* 56:153 (1985).
Feinberg and Bogelstein, *Anal. Biochem.,* 132:6–13 (1983).
Fraser, et al., *In vitro Cell. Dev. Biol.,* 25:225 (1989).
Kunkel, et al., *Methods Enzymol.,* 154:367 (1987).
Labigne-Roussel, et al., *J. Bacteriol.,* 170:1704 (1988).
Harlow & Lane, *Antibodies: A Laboratory Manual,* Cold Spring Harbor Lab. (1988).
Sambrook, et al., *Molecular Cloning: A Lab Manual* (1989) (Table of Contents enclosed).
Sanger, et al., *Proc. Natl. Acad. Sci. U.S.A.,* 71:5463–5467 (1977).
Smith, et al., *Mol. Cell. Biol.,* 3:2156 (1983).
Summers & Smith, *Texas Agri. Exp. Bull. No.* 1555 (1987) (Table of Contents enclosed).
Wright, *Nature,* 321:718 (1986).

DETERMINATION OF NATIVE MOLECULAR WEIGHT OF PEB1 ANTIGEN FROM C. jejuni AND C. coli

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 31 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO:1:

```
Gly Glu Gly Lys Leu Glu Ser Ile Lys Ser Lys Gly Gln Leu Ile Val
 1               5                  10                  15

Gly Val Lys Asn Asp Val Pro His Tyr Ala Leu Xaa Asp Gln Ala
            20                  25                  30
```

( 2 ) INFORMATION FOR SEQ ID NO:2:

( i ) SEQUENCE CHARACTERISTICS:
( A ) LENGTH: 34 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO:2:

```
Asp Val Asn Leu Tyr Gly Pro Gly Gly Pro His Thr Ala Leu Lys Asp
 1               5                  10                  15

Ile Ala Ser Lys Tyr Ser Glu Lys Thr Gly Val Lys Val Asn Trp Asn
            20                  25                  30

Phe Gln
```

ANTISERA AGAINST A PEB1 ANTIGEN FROM CAMPYLOBACTER JEJUNI

This is a continuation of application Ser. No. 07/986,928 filed on Dec. 8, 1992, now abandoned, which is a division of application Ser. No. 07/612,330, filed Nov. 13, 1990, now U.S. Pat. No. 5,200,344.

BACKGROUND OF THE INVENTION

This invention relates to novel antigenic compositions useful in diagnostic testing for the presence of *Campylobacter jejuni* ("*C. jejuni*") or *Campylobacter coli* ("*C. coli*") infection, and useful as vaccines for providing immunological protection against such infection. In certain embodiments, antibodies raised against the novel antigenic compositions may also be used for diagnostic testing for *C. coli* or *C. jejuni*.

*C. jejuni* and *C. coli* are believed to cause both inflammatory and non-inflammatory gastroenteritis (Blaser et al., "*Campylobacter enteritis*," N. Eng. J. Med., 1981; 305:1444–1452). They are recognized as leading causes of inflammatory diarrhea in the U.S. and other developed countries (Blaser et al., *Campylobacter enteritis* in the United States: A Multicenter Study," Ann. Intern. Med., 1983;98:360–365), and are also important causes of endemic diarrheal disease in the developing world (Glass et al., "Epidemiological and Clinical Features of Endemic *Campylobacter jejuni* infection in Bangladesh," J. Infect. Dis., 1983;148:292–296). They have further been recognized as common causes of traveller's diarrhea. Additionally, in the U.S. and other developed countries it has been recognized that *C. jejuni* and *C. coli* are commonly found in many different types of food animals, including cattle, sheep, goats, swine, chickens, ducks and turkeys. Raw milk may be contaminated with *C. jejuni*. Although contaminating organisms are readily killed by pasteurization, many persons consume unpasteurized milk, especially in rural areas. Surface water may be contaminated with *C. jejuni* or *C. coli*, and persons who consume such water may become ill. Commercially raised poultry are particularly susceptible to contamination with these pathogens (Blaser et al., Epidemiology of *Campylobacter jejuni* Infections, *Epidemiologic Reviews*, 1983;5:157–176). Many of the animals used as pets by humans, including dogs, cats, and birds may be infected with these organisms, may become ill as a result of infection, or may transmit the organisms to humans. For all of these reasons, it is important that accurate and rapid diagnostic tests be developed for detection of the infections.

Because *C. jejuni* and *C. coli*, are fastidious to culture, sophisticated and time-consuming techniques are required to isolate and identify these organisms in a microbiology laboratory. Even with optimal technique, the present culture systems may still yield falsely negative culture results. Improved methods for the rapid and accurate detection of *C. jejuni* and *C. coli* infection are needed.

It is known that persons infected with *C. jejuni* or *C. coli* develop antibodies specific to the organisms (Blaser et al., "Human Serum Antibody Response to *Campylobacter jejuni* as Measured in an Enzyme-Linked Immunosorbent Assay", *Infect Immun.*, 1984;44:292–298). Numerous studies have determined that prior *C. jejuni* or *C. coli* infection can be recognized in serological assays. Immunological testing can be inaccurate, however, unless the antigens used include a high concentration of conserved antigens with both a high affinity and a high specificity for the antibodies being detected. The presence of antigens which are not sufficiently unique to attract only *C. jejuni* or *C. coli*-specific antibodies can lead to the formation of non-specific antigen/antibody complexes and therefore to false positive test results. Conversely, antigens which are not common to most *C. jejuni* and *C. coli* strains, or which do not produce strong immunogenic responses to most *C. jejuni* or *C. coli*-specific antibodies may not bind the *C. jejuni* or *C. coli*-specific antibodies of patients infected with certain strains, thus leading to false negative test results. In such cases, the failure of antigen/antibody complexes to form does not necessarily indicate lack of infection but rather an insensitivity of the test system. Adequate sensitivity often coincides with inadequate specificity, and vice-versa.

Studies performed with human volunteers have shown that the prior exposure to experimental *C. jejuni* infection offers some protection against subsequent *C. jejuni* disease. (Black et al., "Experimental *Campylobacter jejuni* Infection in Humans," J. Infect. Dis., 1988;157:472–479; Perlman et al., "Humoral Immune Response to *Campylobacter jejuni* in Human Volunteers," Abstract presented at the 87th Annual Meeting of the American Society for Microbiology, Atlanta, Ga., March 1987; Perlman et al., "Immunity to *Campylobacter jejuni* Following Oral Challenge to Volunteers," Abstract presented at the Fourth International Workshop on Campylobacter Infections, Goreborg, Sweden, June 1987.) Similarly, individuals with prior exposure to unpasteurized milk and high pre-existing levels of anti-*C. jejuni* antibodies have appeared to be at decreased risk of illness when exposed to milk contaminated with *C. jejuni* (Blaser et al., "The Influence of Immunity on Raw-Milk Associated Campylobacter Infections,"*JAMA* 1987;257:43–46.) However, while this work indicates that exposure to whole bacteria may induce a protective host response, the pathogenicity of live *C. jejuni* and *C. coli* limits the utility of a whole cell vaccine. Conversely a vaccine composed solely of purified *C. jejuni* antigens in an appropriate vehicle, or a genetically engineered recombinant vaccine where the *C. jejuni* antigen was presented by an avirulent bacteria or virus, would require use of an antigen capable of inducing the desired immune response in most recipients.

Certain surface proteins of *C. fetus* are disclosed by "Purification and Characterization of a Family of High Molecular Weight Cell Surface Proteins from *Campylobacter fetus,"* Biol Chem., 1988;263:6416–6420.

In Miotti, "Rapid Methods for the Molecular Diagnosis of Infectious Diseases: Current Trends and Applications," Eur. J Epidemiol., 1987; 3:356–364, immunological methods are disclosed for detection of infectious agents, but Miotti does not teach a satisfactory diagnostic test for *C. jejuni* or *C. coli*.

In co-pending U.S. patent application Ser. No. 07/158, 003, filed Feb. 18, 1988, Blaser et al. disclose antigenic compositions for use in detecting antibodies specific for Campylobacter [Helicobacter] pylori.

Outer membrane proteins of *C. jejuni* having molecular weights of 29 kDa, 30 kDa and 31 kDa are discussed In Blaser et al., "*Campylobacter jejuni* outer membrane proteins are antigenic for humans," *Infection and Immunity*, vol. 43, No. 3, pp. 986–93 (March 1984). Several minor proteins (29–31 kDa) were found to be immunogenic by immunoblotting in Dunn et al., "Two-Dimensional Gel Electrophoresis and Immunoblotting of Campylobacter Outer Membrane Proteins," *Infection and Immunity*, vol. 55, No. 7 pp. 1564–72 (July 1987), U.S. Pat. No. 4,404,194 discloses that a 90 kDa protein from *C. jejuni* has immuno-suppressive activity.

U.S. Pat. No. 4,785,086 discloses a DNA probe for detecting *C. jejuni*.

U.S. Pat. No. 4,882,271 discloses a 300–700 kDa antigen from *Campylobacter pylori* and its use in various assays.

SUMMARY OF THE INVENTION

It is an object of the present invention to provide highly specific and highly sensitive diagnostic tests for the presence of *C. jejuni* or *C. coli* infections.

It is another object of the invention to provide antigenic compositions which specifically, and with high sensitivity, attract and bind to antibodies specific to *C. jejuni* or *C. coli*.

It is another object of the invention to provide a procedure to aid in the diagnosis of gastrointestinal symptoms which is relatively non-invasive and causes little patient discomfort.

It is another object of the invention to provide cost-effective clinical diagnostic tests for the presence of *C. jejuni* or *C. coli* which are simple to administer in a clinical or home setting, and which may be quickly evaluated, and to provide kits for performing such diagnostic tests.

It is another object of the invention to provide a protein vaccine which induces high levels of specific antibodies directed against *C. jejuni* and which protects against natural *C. jejuni* infection in humans, livestock, poultry, and other animals.

It is another object of the invention to provide a protein vaccine which induces high levels of specific antibodies directed against *C. coli* and which protects against natural *C. coli* infection in humans, livestock, poultry, and other animals.

It is another object of the invention to provide monoclonal or polyclonal antibodies specific for *C. coli* and/or *C. jejuni*, and methods for their use in detection of *C. coli* and *C. jejuni*.

These and other objects are accomplished by providing the antigenic compositions, vaccines, antisera, methods and kits disclosed herein. In one embodiment of the invention, an antigenic composition comprises at least one of two *Campylobacter jejuni* and *Campylobacter coli*-specific antigens, both of said antigens being obtainable by acid extraction of surface antigens *C. jejuni*, one of said antigens (hereinafter "PEB1" which term includes antigen fragments of the natural protein whether derived from the natural protein or synthetically or recombinantly produced) having an apparent molecular weight of 28 kDa (as measured on sodium dodecyl sulfate polyacrylamide gel under reducing conditions) an apparent molecular weight of 28.9±1.0 kDa (as measured by gel filtration chromatography under native conditions) and an isoelectric point of about 8.5, the other of said surface antigens (hereinafter "PEB3" which term includes antigenic fragments of the natural protein whether derived from the natural protein or synthetically or recombinantly produced) having an apparent molecular weight of 30 kDa (as measured on sodium dodecyl sulfate polyacrylamide gel under reducing conditions), and an isoelectric point greater than 9.3, at least one of said acid extractable antigens being present in said antigenic composition at a concentration higher than that resulting from acid extraction of surface antigens from whole cell *Campylobacter jejuni*. These antigens (PEB1 and PEB3) are highly conserved, and have strong affinity for antibodies induced by most animals' immune response to both *C. coli* and *C. jejuni* infection. The antigens display good specificity, showing low affinity for antibodies other than those specific for *C. jejuni* or *C. coli*. Hence, the antigenic compositions tend to complex with antibodies present in the systems of most *C. jejuni*-or *C. coli*-infected individuals regardless of the specific strain with which such individuals may be infected. Moreover, these antigens are seldom recognized by antibodies present in the body fluids of non-infected individuals.

In preferred embodiments, each acid extractable surface antigen (PEB1 and PEB3) is present in the antigenic composition at a concentration, relative to other acid extractable materials of *C. jejuni*, greater than twice the natural concentration of the antigen resulting from acid extraction, and preferably greater than four times the natural concentration.

Antigenic proteins having substantial homology to said PEB1 and/or PEB3 antigens or their fragments may also be used in accordance with the invention.

PEB1 and/or PEB3 antigens described above may be capable of inducing protective immunity against both *C. jejuni* and *C. coli* when administered to an animal in a non-virulent manner. Hence, the antigens may be used, in combination with a suitable adjuvant, as a vaccine against future *C. coli* or *C. jejuni* infection, both for human and veterinary applications. The vaccination of poultry, for example, may provide the additional benefit of avoiding infection in animals which are consumed by humans, thus avoiding one source of human infection.

Unless expressly stated to the contrary, molecular weights reported herein were calculated from calibration curves based on relative electrophoretic migration of the following molecular weight standards (Bio-Rad) on SDS-PAGE under reducing conditions: lysozyme 14,400 daltons; soybean trypsin inhibitor 1,500 daltons; carbonic anhydrase 31,000 daltons; ovalbumin 45,000 daltons; bovine serum albumin 66,200 daltons; phosphorylase B 97,000 daltons; beta-galactosidase 116,250 daltons; and myosin 200,000 daltons. Sodium dodecyl sulfate polyacrylamide gel (hereinafter "SDS-PAGE") was used in a modified Laemmli gel system as described by Ames in a mini-slab apparatus (Bio-Rad Laboratories, Richmond, Calif.). (Ames GFL, "Resolution of Bacterial Protein by Polyacrylamide Gel Electrophoresis on Slabs," *J. Biol. Chem.*, 1974;249:634–644). 1–2 microgram samples for whole bacterial cells or 50 ng for purified proteins were applied to the gel after boiling for 5 minutes in a buffer containing sodium dodecyl sulfate (hereinafter "SDS"), dithiothreitol and glycerol. The separating gel was 12 percent acrylamide and electrophoresis was performed at 200 volts for about 40 min. at room temperature. Proteins were resolved using the modified silver stain of Oakley et al. (Oakley et al. A simplified ultrasensitive silver strain for detecting proteins in polyacrylamide gels. *Anal. Biochem.*, 1980;105:361–363).

In one aspect of the invention, antigenic compositions containing the PEB1 and/or PEB3 antigens described above are used in methods for the detection of *C. jejuni-* or *C. coli*-specific antibodies. In accordance with these methods, the antigenic compositions of the invention are contacted with samples such as body fluids suspected of containing *C. coli-* or *C. jejuni*-specific antibodies. Following such contacting, known methods are used to determine the extent of formation of an antigen/antibody complex comprised of immunoglobulin bound to antigens from the antigenic composition of the invention. When formation of the complex exceeds a predetermined positive threshold value, the test is positive for presence of *C. jejuni* or *C. coli*-specific antibody.

Preferred techniques for detecting formation of antigen/antibody complexes include, but are not limited to, enzyme-linked immunosorbent assay (ELISA), indirect fluorescence assay, latex agglutination, and liposome-based assay. Alternatively, a Western blot technique may be used, in which case the bands are detected by visual inspection, and substantial appearance of dark bands may be taken as a positive indication.

In one preferred embodiment, for example, the antigenic composition of the invention is immobilized and contacted with the sample to be tested. After washing away the sample and any antibodies therein which did not bind to the immobilized antigenic composition, standard methods are used to determine the extent to which any immunoglobulin remains bound to the immobilized antigens.

The extent of detection of the antigen/antibody complex which should be considered a positive signal (i.e., an indication that the test sample includes *C. jejuni-* or *C. coli-* specific antibody) depends upon the detection means chosen, but may be defined generically as a value greater than the mean plus 1 interval of standard deviation from the results observed from a negative control group, all other parameters (dilution of sample, time of incubation, etc.) being held constant. In some embodiments where higher specificity is desired mean plus two or mean plus three standard deviations may be utilized. The negative control group should consist of asymptomatic individuals who are members of a population which is unlikely to include individuals infected with *C. jejuni* or *C. coli*. A preferred control group, for example, is a group of asymptomatic U.S. children below 10 years of age. Such children form a population unlikely to be infected.

In one aspect of the invention, kits are provided which include both antigenic compositions within the scope of the invention, and which further include means for detecting the presence of any immunoglobulin in a test sample which may become bound to antigens in said composition.

Antisera raised against the PEB1 and/or PEB3 antigen described above may be used in a particularly sensitive and specific test for presence of *C. jejuni* and *C. coli*. Test samples are contacted with such antisera, followed by detection of antibody binding to components of the test sample. Where such binding exceeds a predetermined positive threshold level, the sample is positive for *C. jejuni* or *C. coli*. The threshold is determined as described above. Kits containing such antisera and means for detecting such antibody binding provide a convenient means of practicing the test.

BRIEF DESCRIPTION OF THE DRAWINGS

FIG. 7 shows part of the regression curve including MW standards of 150, 29, and 12.4 kDa. PEB1 antigen eluted immediately after carbonic anhydrase (29 kDa) with a calculated MW of 28.9±1.0 kDa.

DETAILED DESCRIPTION OF THE PREFERRED EMBODIMENTS

A *C. jejuni* strain, denoted by the inventors' I.D. No. 81-176 was originally isolated from a human child during an outbreak of *C. jejuni* diarrheal disease and has been shown to be virulent in studies with human volunteers and non-human primates. The strain has been maintained frozen at −70° C. in brucella broth (BBL Microbiology Systems, Cockeysville, Md.) containing 15% glycerol. It was deposited with the American Type Culture Collection (ATCC) 12301 Parklawn Drive, Rockville, Md. 20852 U.S.A. on Apr. 3, 1990 and has been accorded ATCC Designation 55026. The strain is referred to herein as the "Deposited Strain". Permanence of the deposit and ready accessibility thereto is provided in accordance with U.S. patent law, the Budapest Treaty, and other applicable laws and regulations. The deposit will be accessible to the public on and after the date of issuance of any U.S. patent arising from the present patent application which refers to the deposit.

All restrictions upon availablility of the deposited strain will be irrevocably removed upon granting of any U.S. patent arising from the present application.

The PEB1 and PEB3 antigens from the deposited strain are found in all *C. jejuni* strains we have tested—not just the deposited strain—and each is useful in the antigenic composition of the invention regardless of the source from which it is derived, including derivation from *C. coli*.

The Deposited Strain was grown on trypticase soy agar with 5% sheep blood (PASCO, Wheat Ridge, Colo.) in a microaerobic atmosphere (5% oxygen, 10% carbon dioxide and 15% nitrogen) at 37° C. for 24 h for three generations. Protein concentrations were measured using the Markwell et al. modification of the Lowry method for crude surface protein (Markwell et al. A modification of the Lowry procedure to simplify protein determinations in membrane and lipoprotein samples. *Anal. Biochem.*, 1978;87:206–210.), and using Quantigold (Diversified Biotech, Newton Center, Mass.) for the purified proteins.

Figure 1:
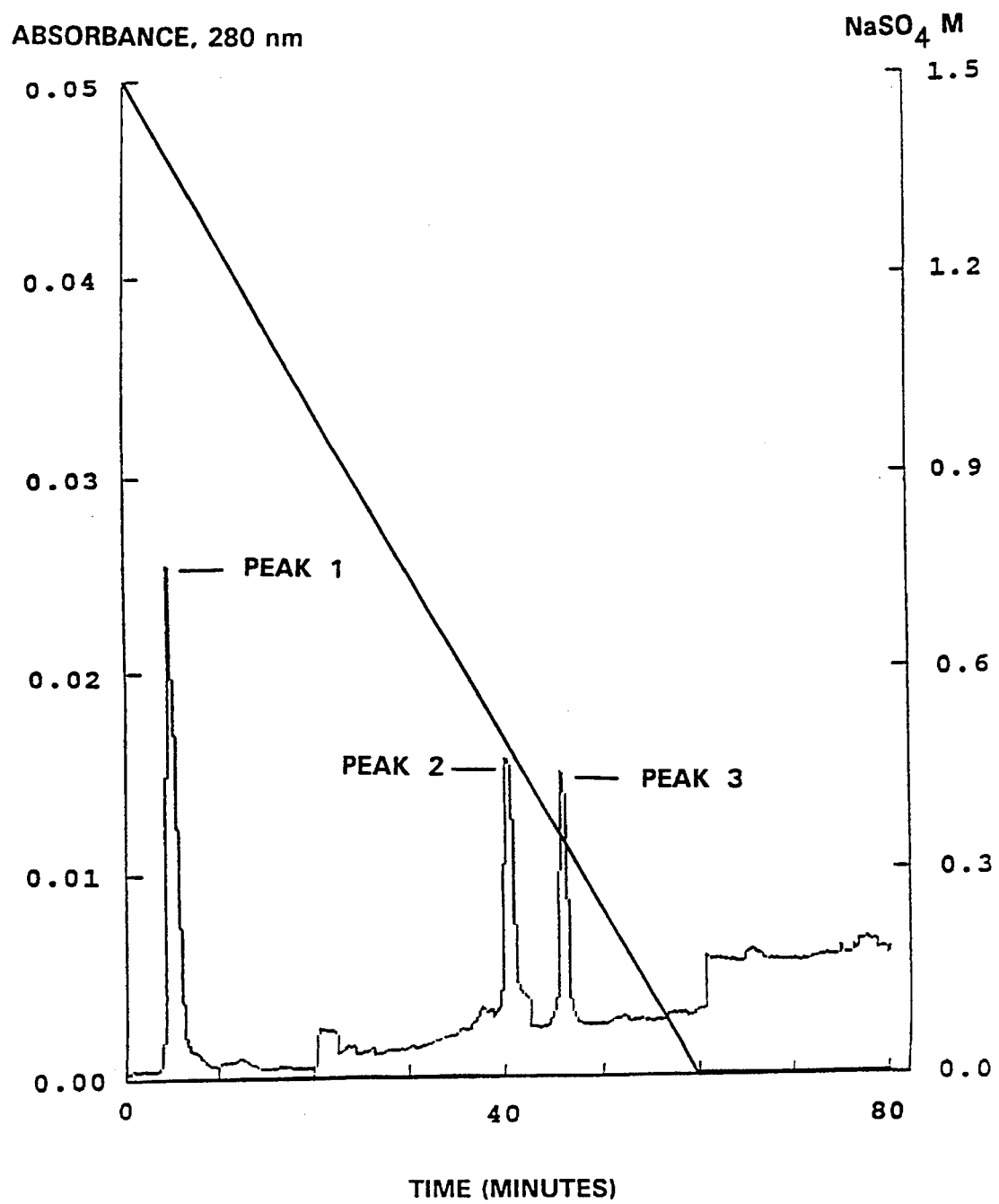
FIG. 1 is a graph of protein elution over time (and of decreasing sodium sulfate concentration) from hydrophobic interation FPLC on a phenyl-Superose column (Pharmacia), used for purifying PEB1 antigen from *C. jejuni* strain 81-176. Conditions for purification are as described in the text. Fractions of eluted materials were collected every 2 minutes and were checked for the presence of PEB1 antigen by SDS-PAGE. Peak 2 contained a mixture of PEB3 and PEB4 antigens, and Peak 3 contained PEB1 antigen with greater than 98% purity.
Figure 2:
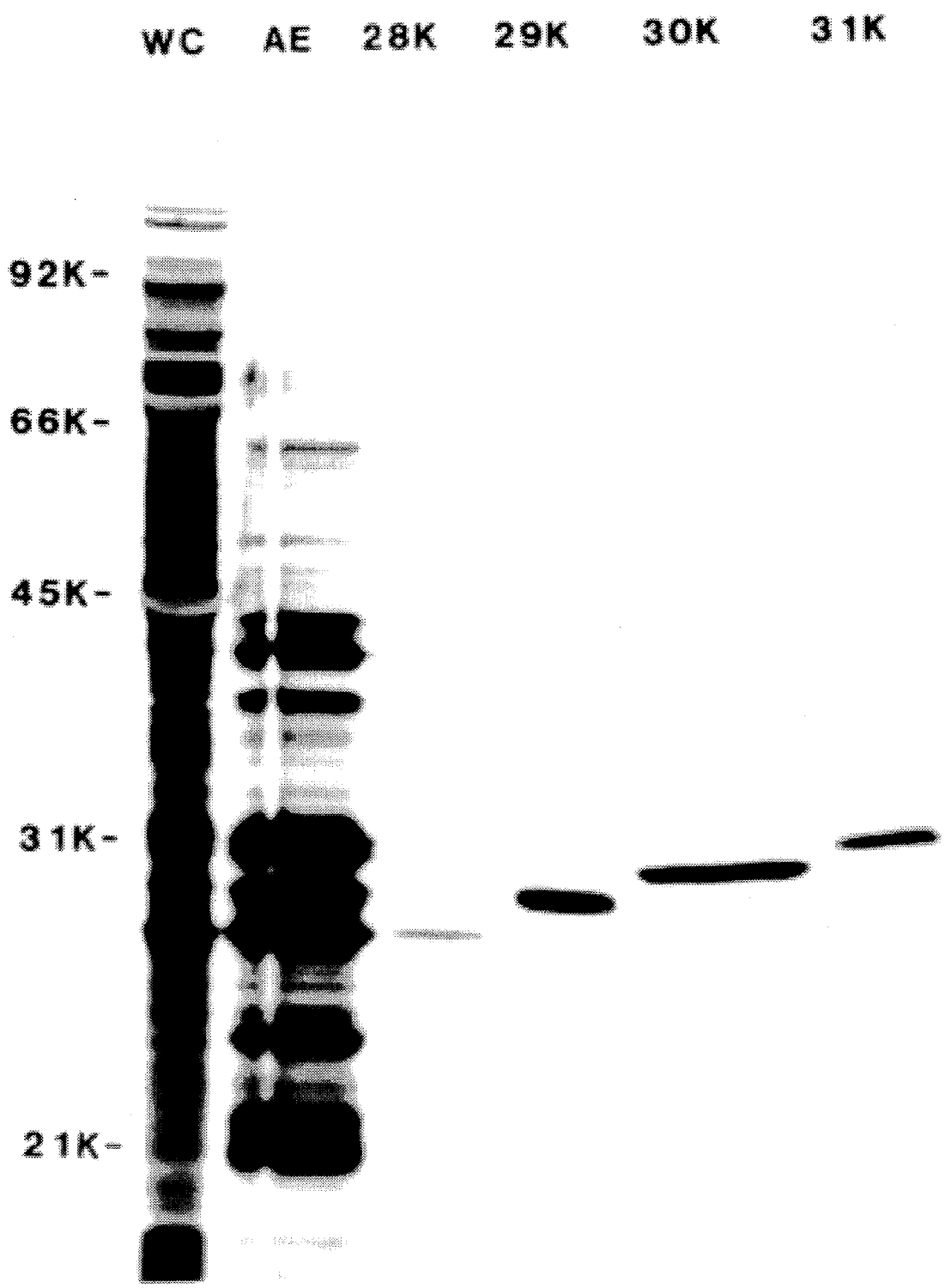
FIG. 2 is a photograph of protein bands following electrophoresis on SDS-PAGE of purified *C. jejuni* proteins from strain 81-176. Lanes are whole bacterial cells(WC), acid extract(AE), PEB1(28K), PEB2(29K), PEB3(30K) and PEB4(31K) antigens. Molecular weight markers are shown at left.

Cells were harvested and washed twice with distilled water by centrifugation at 3500×g for 15 min. To prepare a crude mixture of surface structures, the bacterial cells were suspended in 0.2M glycinehydrochloride buffer, pH 2.2, at a concentration of 0.1 g (wet weight) of cells to 2.5 ml of buffer. Suspensions were stirred at 25° C. for 15 min. and then centrifuged at 11,000×g for 15 min., the supernatant was retained, and the pH was neutralized with sodium hydroxide. The preparation was lyophilized and reconstituted with distilled water. The salt in this preparation was removed using a Sephadex G-15 column (Pharmacia, Piscataway, N.J.) with distilled water as running buffer. The crude mixture was centrifuged at 1,000×g for 15 minutes to pellet any insoluble material. For final purification of PEB1, the supernatant was separated by hydrophobic interaction chromatography performed on a phenyl-superose column (Pharmacia LKB Biotechnology Inc. Piscataway, N.J.) using an FPLC system (Pharmacia). The initial buffer was pH 8.9, 20 mM boric acid, 1.5M $Na_2SO_4$ at a flow rate of 0.25 ml/min. A linear gradient with pH 8.9, 20 mM boric acid was performed to 0% of $Na_2SO_4$ over 60 minutes and the column eluate monitored for UV absorbance at 280 nm to define protein peaks (FIG. 1). The fractions of protein eluted were checked for the presence of the 28 kilodalton (kDa) protein band using SDS-PAGE analysis (FIG. 2). It was found that the 28 kDa protein (PEB1) eluted between about 44 and 50 minutes at a sodium sulfate concentration of about 390 mM (FIG. 1).

For purification of PEB3 antigen, the acid extracted material was separated by cationic exchange FPLC chromatography on a Mono S column (Pharmacia). The running buffer was 50 mM HEPES, pH 9.3 at a flow rate of 1.0 ml/min and the concentration of NaCl was increased linearly from 0 to 400 mM over 20 minutes. Each fraction was checked by SDS-PAGE for the presence of PEB3 migrating at 30 kDa. The PEB3 antigen eluted from the column at about 200 mM NaCl. The fraction containing partially purified PEB3 was purified to homogeneity on the phenyl-Superose column using the same conditions as described above for the purification of the PEB1 antigen. PEB3 eluted from this column at around 450 mM $Na_2SO_4$. Purified PEB3 (30 kDa) is shown in FIG. 2.

Determination of the isoelectric point (pI) of the protein antigen was made by isoelectric focusing in RESOLVE™ (thin layer agarose gels) with pH ranging between 3 and 10 using the RESOLVE-HB kit (Isolab Inc., Akron, Ohio) and the silver stain of Willoughby and Lambert (Willoughby et al. "A Sensitive Silver Stain for Proteins in Agarose Gels," *Anal Biochem.*, 1983;130:353–358). An experient formula of pI versus migration distance was generated by using 3 standard proteins of known pI between 6.8 and 9.3. These standard proteins were trypsinogen [pI=9.3], L-lactic dehydrogenase [pI=8.3, 8.4, and 8.6 (3 subunits)], and myoglobin [pI=6.8 and 7.2 (2 subunits)]. For the PEB1 antigen, the pI was found to be about 8.5, and for the PEB3 antigen, the pI was greater than 9.3.

The purified proteins were prepared for amino acid analysis and sequencing by dialysis against water and lyophilization. Amino acid analysis was performed using the method of Jones (Jones B. N., "Amino Acid Analysis and Enzymatic Sequence Determination of Peptides by an Improved o-phthaldialdehyde Precolumn Labeling Procedure," *J. Liq. Chromatogr.*, 1981;4:565– 568). It was found that each of these proteins contained a large percentage of basic amino acids as shown below in Table 1:

TABLE 1

AMINO ACID COMPOSITION OF
PEB1 AND PEB3 ANTIGENS OF *C. jejuni*

| Amino Acid | Mole % | |
|---|---|---|
| | PEB 1 | PEB 3 |
| Polar | | |
| Lysine | 30.2 | 22.9 |
| Histadine | 0.6 | 1.4 |
| Arginine | 2.0 | 4.0 |
| Asparagine/Aspartate | 11.1 | 11.9 |
| Glutamine/Glutamate | 6.6 | 7.5 |
| Serine | 3.8 | 4.6 |
| Threonine | 4.4 | 6.7 |
| Nonpolar | | |
| Valine | 5.5 | 5.4 |
| Methionine | 0.4 | 1.5 |
| Isoleucine | 5.2 | 6.0 |
| Leucine | 7.4 | 5.1 |
| Alanine | 9.4 | 9.3 |
| Phenylalanine | 3.3 | 4.6 |
| Tryptophan | not determined | |
| Proline | not determined | |
| Glycine | 6.7 | 6.3 |
| Cysteine | 0 | 0 |
| Tyrosine | 3.5 | 2.8 |

Amino acid sequencing was performed on an Applied Biosystems 470 A Protein Sequencer equipped with the 120A Autoanalyzer using the 03RPTH program. 30 of the first 31 amino acid residues of the amino terminus of PEB 1 and the 34 amino-terminus acids of PEB 3 were defined as shown in Table 2:

TABLE 2

AMINO TERMINAL SEQUENCE OF PEB1 AND PEB3 FROM C. JEJUNI 81-176

|  | 1 |  |  |  | 5 |  |  |  |  | 10 |  |  |  |  | 15 |  |  |  |  |
|---|---|---|---|---|---|---|---|---|---|---|---|---|---|---|---|---|---|---|---|
| PEB1 SEQ. ID. NO: 1) | Gly | Glu | Gly | Lys | Leu | Glu | Ser | Ile | Lys | Ser | Lys | Gly | Gln | Leu | Ile |  |  |  |  |
| PEB3 SEQ. ID. NO: 2) | Asp | Val | Asn | Leu | Tyr | Gly | Pro | Gly | Gly | Pro | His | Thr | Ala | Leu | Lys |  |  |  |  |
|  |  |  |  |  | 20 |  |  |  |  | 25 |  |  |  |  | 30 |  |  |  |  |
| PEB1 | Val | Gly | Val | Lys | Asn | Asp | Val | Pro | His | Tyr | Ala | Leu | — | Asp | Gln | Ala |  |  |  |
| PEB3 | Asp | Ile | Ala | Ser | Lys | Tyr | Ser | Glu | Lys | Thr | Gly | Val | Lys | Val | Asn | Trp | Asn | Phe | Gln |

Any sample suspected of containing *C. jejuni* or *C. coli* antibodies may be tested in accordance with the methods set forth herein. Preferably, the samples to be tested are bodily fluids such as blood, serum, urine, tears, saliva and the like. Both medical and veterinary applications are contemplated. In addition to human samples, samples may be taken from poultry or mammals such as non-human primates, horses, swine, etc. Due to the sensitivity of the test described, it is possible to dilute the sample prior to testing. Dilution may proceed by addition of any fluid compatible with each of the sample, the antibodies to be tested, and the antigenic composition. Serum, when used as the sample, may, for example, be diluted with one or more fluids selected from the group consisting of phosphate-buffered saline, pH 7.0–7.4 (hereinafter, "PBS") PBS-containing Tween 20 (hereinafter, "PBS T"), PBS T with thimerosal (hereinafter, "PBS TT") PBS TT (gelatin) (hereinafter, "PBS TTG"), and PBS TTG with bovine gamma globulin (hereinafter, "PBS TTGG") Dilutions, when testing for IgG antibody, may be as high as a ratio from about 1:00 to about 1:1000, such as, for instance, about 1:800. When testing for IgA antibody, sample may be diluted, for example, about 1:25 to about 1:200, such as 1:100, and for IgM antibody, about 1:50 to about 1:800 (e.g. 1:200). IgG tests are preferred.

Preferred diluents and dilution ratios may vary according to the sample being tested. Urine, for instance, is already relatively dilute and may not need to be diluted further. However, it may not be necessary to concentrate urine as is often necessary with other assays. Prior to testing, the pH of urine is preferably adjusted to between about 7.0 and 7.4, the preferred pH for antibody function.

While dilution of sample is not required, it is believed that dilution reduces the possibility that significant antigen/antibody complexes will be formed in the absence of *C. jejuni*- or *C. coli*-specific antibodies. The extent of dilution should be taken into account in adjusting the threshold level of antigen/antibody complex which should be considered a positive signal.

While the present disclosure provides an easy method for obtaining the preferred antigens from the deposited *C. jejuni* strain, it is emphasized that these antigens are common to a large number of *C. jejuni* strains as shown by their efficacy in testing for the existence of *C. jejuni*. While the deposited strain and the description of the present specification provide an easy manner of isolating these antigens, it is emphasized that the present invention broadly encompasses use of these antigens regardless of the source from which they are derived.

Before contacting a test sample with antigenic compounds in accordance with the invention it is preferred (but not necessary) that the antigenic composition be immobilized using conventional techniques. In one alternative embodiment, liposome-based assays may be used as described in more detail below. For conventional immoblization, polystyrene plates, for example, may be incubated with antigenic suspensions made in accordance with the invention. Alternatively, for example, antigens isolated as protein bands on electrophoretic gel may be transferred to a nitrocellulose sheet by known methods (See Example 3). See Towbin et al., *Proc. Nat'l. Acad. Sci.*, 76: 4350–54 (1979); Burnette et al., *Biochem.*, 112: 195–203 (1981). Numerous other techniques are known in the art for binding antigens to substantially inert substrates.

Bound antigens in accordance with the invention are preferably contacted with a dilute fluid which includes the sample to be tested for presence of antibody to *C. jejuni/C. coli*. The antigen and sample are preferably incubated for at least 5 to 15 minutes. Less time is needed when incubation proceeds at or near human body temperature, about 37° C. Incubation at other temperatures, for instance 4° C., is also proper, but generally requires additional incubation time. Preferred incubation time at 37° C. is from about 5 minutes to about 90 minutes. The bound antigens should then be rinsed to remove any unbound antibodies, i.e., those which are not specific for the antigens. Preferably, rinsing proceeds with a buffer solution such as PBS T, PBS TT or Tris/Tween/ Sodium chloride/azide. Multiple rinsings are preferred.

During incubation, *C. jejuni*-specific antibodies bind to the immobilized antigens to create antigen/antibody complexes. All unbound antibodies are substantially removed during the rinsing procedure. Due to the high specificity of the antigens of the invention, antibodies which are not specific for *C. jejuni/C. coli* are substantially removed by the rinsing. Naturally, if the tested sample did not contain *C. jejuni/C. coli*-specific antibodies, the immobilized antigens would be substantially free of human antibody, and subsequent testing for antigen/antibody complexes should not indicate a substantial presence of such complexes. On the other hand, if the tested sample were rich in *C. jejuni/C. coli*-specific antibodies, these antibodies should have bound to the immobilized antigens to form a large quantity of antigen/antibody complex for subsequent detection.

Detection of antigen/antibody complex may be achieved by a wide variety of known methods. Preferred methods include but are not limited to enzyme-linked immunosorbent assay, latex agglutination, Western-blot technique or indirect immunofluorescence assay.

Typically, the *C. jejuni/C. coli*-specific antibodies complexed with immobilized antigen are detected by contact with labelled or otherwise detectable second antibodies specific for the immunoglobulin being tested for. If the test sample is human sera, for example, the detectable second antibody is specific for human immunoglobulin. The labelled second antibodies may be specific for any human antibody, preferably of the IgG or IgA type, most preferably IgG. When acute sero-conversion is suspected, an IgM test using a labelled second antibody specific for IgM may be appropriate. The second antibodies are preferably incubated with the immobilized antigens for about 5 minutes to about 2 hours, preferably 30 minutes to 60 minutes at a temperature of about 20° C. to about 37° C. Then, the antigens are washed with a buffer solution (preferably multiple times) in order to remove all unbound labelled antibody. The washings will remove substantially all labelled antibody except that which has bound to immunoglobulin present on the antigens. Of course, substantially the only human immunoglobulin present at this point should be *C. jejuni-* or *C. coli*-specific antibody. Hence, the presence of *C. jejuni-* or *C. coli*-specific antibody may be indirectly measured by determining the presence or absence of the labeled second antibody.

There are many known techniques for detecting the label, which vary with the type of label used. For instance, fluorescein-labelled antibody may be detected by scanning for emitted light at the characteristic wavelength for fluorescein. Alternatively, an enzyme label is detected by incubation with appropriate substrate and detection of an enzymatic activity, preferably activity resulting in a color change. Such activity can be determined by visual inspection or can be read automatically by a spectrophotometer set at the appropriate wavelength.

For example, the enzyme label may be horseradish peroxidase and the substrate may be $H_2O_2$ and 2,2'-azinobis(3-ethylbenzothiazoline-6-sulfonic acid) which produces in the presence of the enzyme, a compound detectable by a spectrophotometer set at 414 nm.

In Western blotting, the positive signal may be detected when an enzyme is conjugated to the second antibody. Incubation with appropriate substrate enzymatically produces a color product in the immediate vicinity of the antigenic band resolved by this process. The presence of a reactive band may be detected by visual inspection. See the procedure described in Example 3. In an indirect immunofluorescence assay, fluorescein-labeled second antibodies may be detected by fluorescence-activated detectors, or by visual inspection.

A liposome-based assay may involve the presence of fluorescein, an enzyme or a substrate inside a liposome onto whose surface *C. jejuni* antigens are expressed. These liposomes are incubated with a diluted body fluid sample to be tested, and are thoroughly washed. Any liposomes with immunoglobulins on their surface forming an antigen/antibody complex may be recognized by attaching a second antibody, specific to the immuniglobulin being tested for, onto the inside walls of a polystyrene tube containing the liposomes. Liposomes having antibody bound to their surfaces will become immobilized on the tube walls, and non-immobilized liposomes will be washed away. The liposomes can by lysed with, for instance, detergent, or complement, and the enzyme or subtrate that was in the interior is now free to react with the complementary substrate (or enzyme) in the solution in the tube. Enzymatic activity, preferably a color change reaction could be detected by visual inspection or spectrophotometric color determination. Enzymatic activity beyond the predetermined positive threshold indicates the presence of *C. jejuni* or *C. coli* specific antibodies.

Testing, of the invention with rabbit antiserum raised to strains not used in preparation of the antigenic mixture (heterologous) indicated that the antigenic composition could detect antibodies raised to these strains, as well as detecting antibodies raised to the homologous strain. This indicated that the antigenic composition included conserved antigens and had the type of broad specificity which should be useful in serologic assays.

The sensitivity and specificity of the antibody detection in accordance with the present invention have been determined using serum obtained from persons from defined populations. Example 1 is illustrative of the results of this assessment.

The invention is futher elucidated by reference to the following examples which are set forth only as non-limiting illustrations of the invention.

EXAMPLE 1

Determination of the Antigenicity of the PEB1 and PEB3 Proteins for Infected Humans Using an ELISA The purified PEB1 and PEB3 proteins were compared with a crude acid-extracted mixture of *C. jejuni* proteins as antigens recognized by humans with diarrheal diseases. The ELISA system substantially followed the teachings of Blaser et al. (Blaser et al., "Human serum antibody response to *Campylobacter jejuni* as measured in an enzyme-linked immunosorbent assay," *Infect. Immun.*, 1984;44:292–298) to detect human serum IgG, except certain details were changed as described below.

To sensitize ELISA plates (Nunc, Inc., Naperville, Ill.), purified proteins and the crude surface protein preparation were diluted in 0.015M carbonate buffer, pH 9.6. One hundred ul of these preparations were added to each well, and the plates incubated at 4° C. overnight. The plates were washed once with 0.01M PBS, pH 7.2, in 0.03% Tween-20 and 0.01% thimerosal (PBS-T-T) and were blocked with 200 ul/well of 0.1% gelatin in PBS-T-T overnight at 4° C. The plates were then washed twice with PBS-T-T, and 100 ul of antisera diluted with 0.5% bovine gamma globulin and 0.1% gelatin in PBS-T-T was added to each well. After a 1 hour incubation at 37° C., the plates were washed four times as before, and 100 ul of peroxidase-goat-anti-human IgG (1:500, Boehringer Mannheim Biochemical, San Diego, Calif.) or 100 ul of peroxidase goat-anti-rabbit IgG (1:5000) diluted with 0.1% bovine gamma globulin and 1% BSA in PBS-T-T was added to each well and incubated at 37° C. for 1 hour. The plates were washed six times, 100 ul of peroxidase developer (20 mg of 2,2'-azinobis[3-ethylbenzothiazoline- 6-sulfonic acid], 34 ul of $H_2O_2$, 9.35 ml of 0.2 M $Na_2HPO_4$, and 10.65 ml of 0.1M citric acid) was added to each well, and the product of the peroxidase reaction determined after 15 minutes for human antibodies and 30 minutes for rabbit antibodies at room temperature using a MR 600 microplate reader (Dynatech Laboratories Inc., Alexandria, Va.) at 414 nm. 20 ng of antigen was used. Optical densities per well from acute and convalescent sera were compared. Seroconversion was defined as an Optical density 414 value in convalescent serum greater than 50% that in acute serum. Seroconversion in 19 patients with sporadic cases of acute *C. jejuni* or *C. coli* diarrhea is shown below in Table 3:

TABLE 3

Seroconversion[a] to
*C. jejuni* proteins of Campylobacter-infected
persons and persons with other diarrheal diseases

| Patient isolate | AE[b] | PEB1[c] | PEB2[d] | PEB3[e] | PEB4[f] |
|---|---|---|---|---|---|

*Campylobacter*

TABLE 3-continued

Seroconversion[a] to
C. jejuni proteins of Campylobacter-infected
persons and persons with other diarrheal diseases

| Patient isolate | AE[b] | PEB1[c] | PEB2[d] | PEB3[e] | PEB4[f] |
|---|---|---|---|---|---|
| *jejuni/coli* | | | | | |
| 1 C. coli | + | + | − | + | − |
| 2 C. coli | + | + | − | + | + |
| 3 C. jejuni | −[g] | + | − | −[g] | + |
| 4 C. coli | −[g] | −[g] | −[g] | −[g] | −[g] |
| 5 C. jejuni | − | − | − | + | − |
| 6 C. jejuni | + | + | − | + | + |
| 7 C. jejuni | + | + | − | + | − |
| 8 C. coli | + | + | − | + | − |
| 9 C. jejuni | + | + | − | + | − |
| 10 C. jejuni | + | + | −[g] | + | − |
| 11 C. coli | + | + | − | + | − |
| 12 C. jejuni | + | + | + | + | + |
| 13 C. jejuni | + | + | − | + | − |
| 14 C. jejuni | + | + | − | + | + |
| 15 C. jejuni | − | − | − | + | − |
| 16 C. jejuni | + | + | − | + | − |
| 17 C. jejuni | + | + | + | + | + |
| 18 C. jejuni | + | + | − | − | − |
| 19 C. jejuni | −[g] | − | − | −[g] | − |
| % seroconversion | 73.7 | 78.9 | 10.5 | 78.9 | 31.6 |
| Other pathogens | | | | | |
| 1 Shigella | − | − | − | − | − |
| 2 Salmonella | − | − | − | − | − |
| 3 Shigella | − | − | − | − | − |
| 4 Yersinia | − | − | − | − | − |
| 5 Salmonella | − | − | − | − | − |
| % seroconversion | 0 | 0 | 0 | 0 | 0 |
| No pathogens identified | | | | | |
| 1 | − | − | − | − | − |
| 2 | − | − | − | − | − |
| 3 | − | − | − | − | − |
| 4 | − | − | − | − | − |
| 5 | − | − | − | − | − |
| % seroconversion | 0 | 0 | 0 | 0 | 0 |

[a] Patients had acute diarrheal illnesses for which they sought attention at medical facilities in Denver. Acute phase sera were obtained within seven days of illness onset and convalescent sera were obtained 11 to 40 days later. Seroconversion is defined as O.D$_{414}$ value increase by at least 50% in convalescent serum compared wth that in acute serun. Value in Convalescent serun must be greater than 0.200. + = seroconversion, − = no seroconversion.
[b] Antigen was extracted from C. jejuni strain 81-176 in glycine buffer (pH 2.2) as described above (Acid extract).
[c] PEB1 antigen was purified to homogeneity fron acid extract through hydrophobic interaction FPLC.
[d] PEB2 antigen was purified to homogeneity from acid extract through sequential cationic exchange, hydrophobic interaction, and gel filtration FPLC.
[e] PEB3 antigen was purified to homogeneity from acid extract through sequential cationic exchange and hydrophobic interaction FPLC.
[f] PEB4 antigen was purified to homogeneity from acid extract through sequential cationic exchange and gel filtration FPLC.
[g] O.D. value greater than 1.000 in both acute and convalescent serum.

EXAMPLE 2

Use of Specific Antiserum to the PEB1 C. jejuni
Protein Antigen in the Detection of Strains of C.
jejuni and C. coli We examined the potential application of an antisera to the C. jejuni PEB1 protein in the identification of C. jejuni and C. coli. Preparation of antisera and peformance of the ELISA followed previously described methods and as described in Example 1. Antisera against the mixture of acid-extracted proteins, and the purified PEB1 protein, were raised in adult New Zealand white female rabbits by three subcutaneous injections at 2-week intervals of 5 ug of purified protein in 1 ml of an equivolume mixture of antigen and adjuvant (67% of 0.1M PBS at pH 7.2, 27% hexadecane, 6% glycerol). Fresh normal sera from the same rabbits were obtained prior to inoculation. Thirty-five strains of C. jejuni, 15 of C. coli, 10 of C. fetus, 5 of Campylobacter laridis and 5 of Helicobacter pylori (formerly known as C. pylori) were used in this study. The strains had been maintained frozen at −70° C. in brucella broth containing 15% glycerol. For preparation of antigens, the cells were grown overnight on blood agar plates, and harvested with cotton swabs and resuspended in water. Protein concentrations were determined using the Markwell et al. modification of the Lowry method; concentrations were adjusted to 1 ug/ml in water.

Whole bacterial cells (0.5 ug protein/well) were then used in an IgG ELISA. The specific antisera were absorbed with whole *Escherichia coli* bacterial cells, diluted 1:500 for antiserum to PEB1 and the mixture of acid-extracted proteins, and tested in the ELISA system with an O.D. value greater than 0.1 at 414 nm. defined as positive. In this system normal rabbit serum did not recognize any of the Campylobacter strains, as expected (Table 4). In contrast, the antisera to the mixture of acid-extracted proteins recognized all 35 C. jejuni strains, all 15 C. coli strains, 9 of 10 C. fetus strains, all 5 C. laridis strains, and 2 of 5 H. pylori strains. The antiserum to the PEB1 protein recognized all 35 C. jejuni strains, and all 15 C. coli strains, but none of the other Campylobacter or Helicobacter isolates (Table 4 and FIG. 3). Thus, the antisera to the PEB1 protein appeared to have the greatest discriminatory power, having both 100% sensitivity and specificity for C. jejuni and C. coli.

TABLE 4

RECOGNITION OF CAMPYLOBACTER
AND HELICOBACTER CELLS
IN AN ELISA BY ANTISERA TO *C. JEJUNI* PROTEINS

| | % of Bacterial Strains Positive[d] | | | | |
|---|---|---|---|---|---|
| Antisera | C. jejuni (n = 35) | C. coli (n = 15) | C. fetus (n = 10) | C. laridis (n = 5) | H. pylori (n = 5) |
| NRS[a] | 0 | 0 | 0 | 0 | 0 |
| anti-AE[b] | 100 | 100 | 90 | 100 | 40 |
| anti-PEB1[c] | 100 | 100 | 0 | 0 | 0 |

[a] Normal rabbit serum absorbed with E. coli bacterial cells
[b] Antisera from adult NZW rabbits hyperimmunized with pooled acid-extracted C. jejuni antigens as described in the methods section above, subsequently absorbed with E. coli bacterial cells
[c] Antisera from adult NZW rabbits hyperimmunized with the purified PEB1 antigen (prepared as described above) as described in the methods sections above, subsequently absorbed with E. coli bacterial cells
[d] All bacterial strains used were clinical isolates of *Campylobacter* and *Helicobacter* species that had been stored at −70° C. prior to subculture and testing.

EXAMPLE 3

Detection of PEB1 Antigen in Whole Bacterial
Cells by Western Blot

Figure 3:
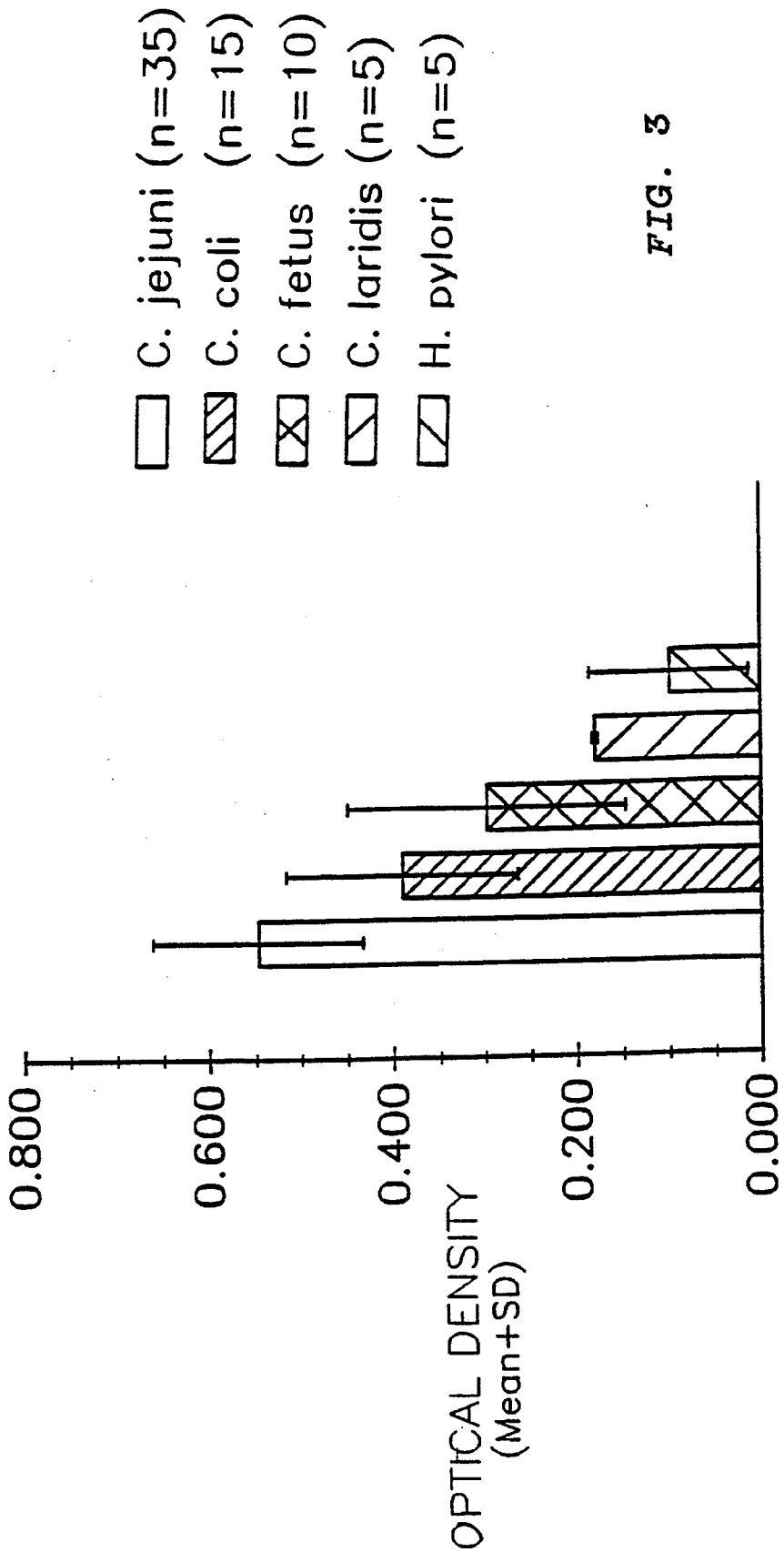
FIG. 3 is a graph showing recognition of Campylobacter and Helicobacter by antisera to *C. jejuni* proteins, by ELISA. Whole bacterial cells were used as antigens. First antibodies were rabbit anti-acid extract. $O.D_{414}$ value greater than 0.1 was defined as positive.
Figure 4:
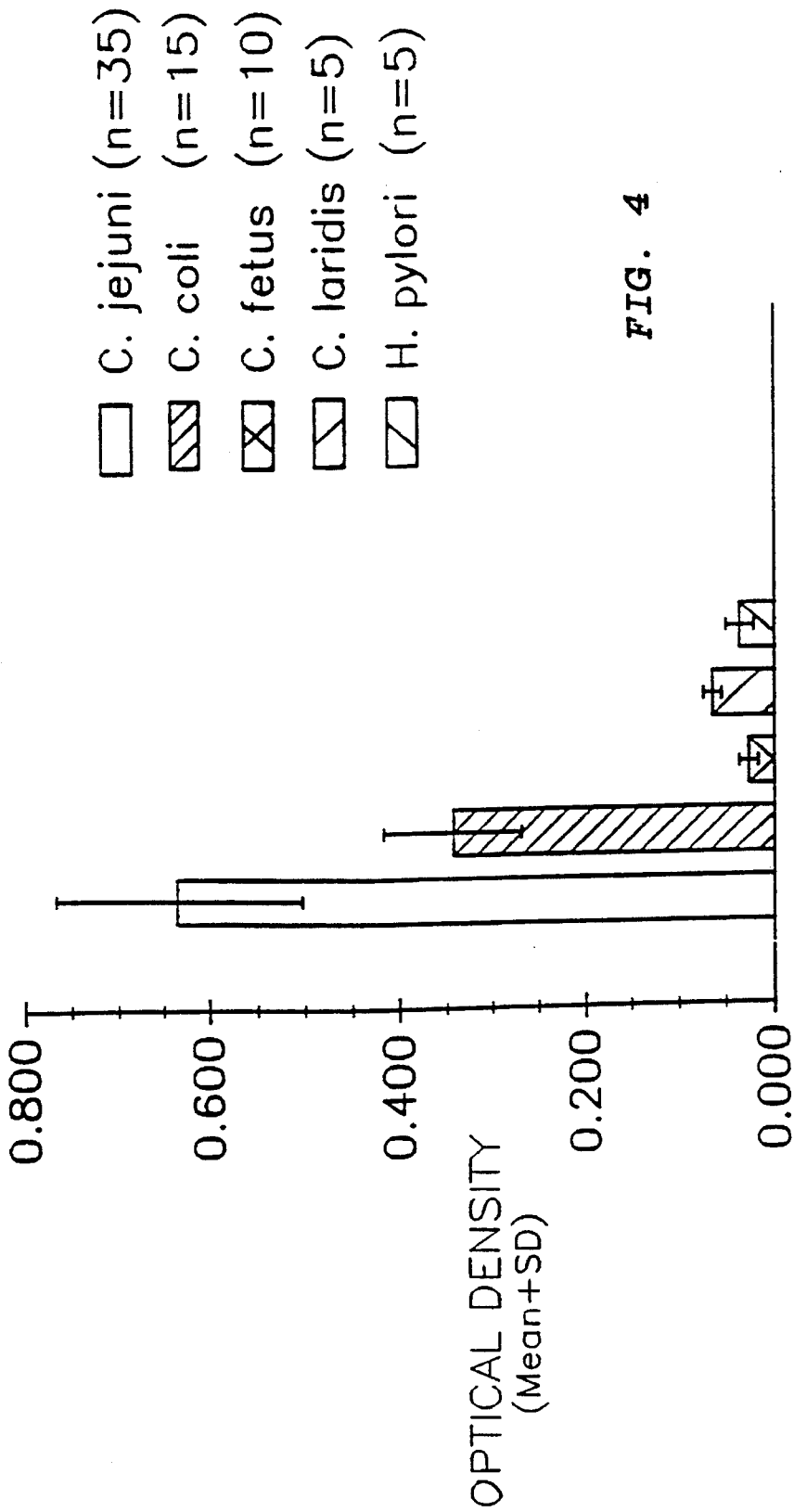
FIG. 4 is a graph showing recognition of Campylobacter and Helicobacter by antisera to *C. jejuni* proteins, by ELISA. Whole bacterial cells were used as antigens. First antibodies were rabbit anti-PEB1 antigen. $O.D_{414}$ value greater than 0.1 was defined as positive.
Figure 5:
FIG. 5 is a Western blot of anti-PEB1 against representative Campylobacter and Helicobacter strains. The antigens used are whole cells prepared as described in EXAMPLES 2 and 3. Bacterial strains of *C. jejuni* (except strains 81-176, 81-93 and 81-94), *C. coli* and *C. laridis* had been identified by DNA hybridization. The *C. fetus* strains were identified by the presence of high molecular weight surface array proteins detected by SGS-PAGE and Western blot (Z. Pei and M. Blaser J. Clin. Invest. 86:1036–1043, 1990). The method for the Western blot is as described in the text. The arrow indicates 28 kDa bands, which were found in all *C. jejuni* (strains 81-176, 81-93, 81-95, D996 and D1916, lanes a through e) and all *C. coli* (strains D743, D1035, D130, D126 and D115, lanes f through j) strains, but not found in any of *C. laridis* (strains D459 and D1014, lanes k and l), *C. fetus* (strains 84-32 and 80-109, lanes m and n) strains, or in *H. pylori* strain (strain 16-IIA, lane o).
Figure 6:
FIG. 6 is a Western blot of anti-PEB1 against proteinase K-digested whole cells and glycine extract from *C. jejuni* and *C. coli*. Whole bacterial cells of two *C. jejuni* (strains 86-64 and 86-223, lanes e, f, g and h) and glycine extract of *C. jejuni* (strain 81-176, lanes i and j) was used in this study. Lanes a, c, e, g and i containes samples that were incubated with $H_2O$ (control); lanes b, d, f, h and j contained samples that were incubated with proteinase K. For the samples incubated with proteinase K the 28 kDa band, as shown by the arrow, disappeared.
Figure 7:
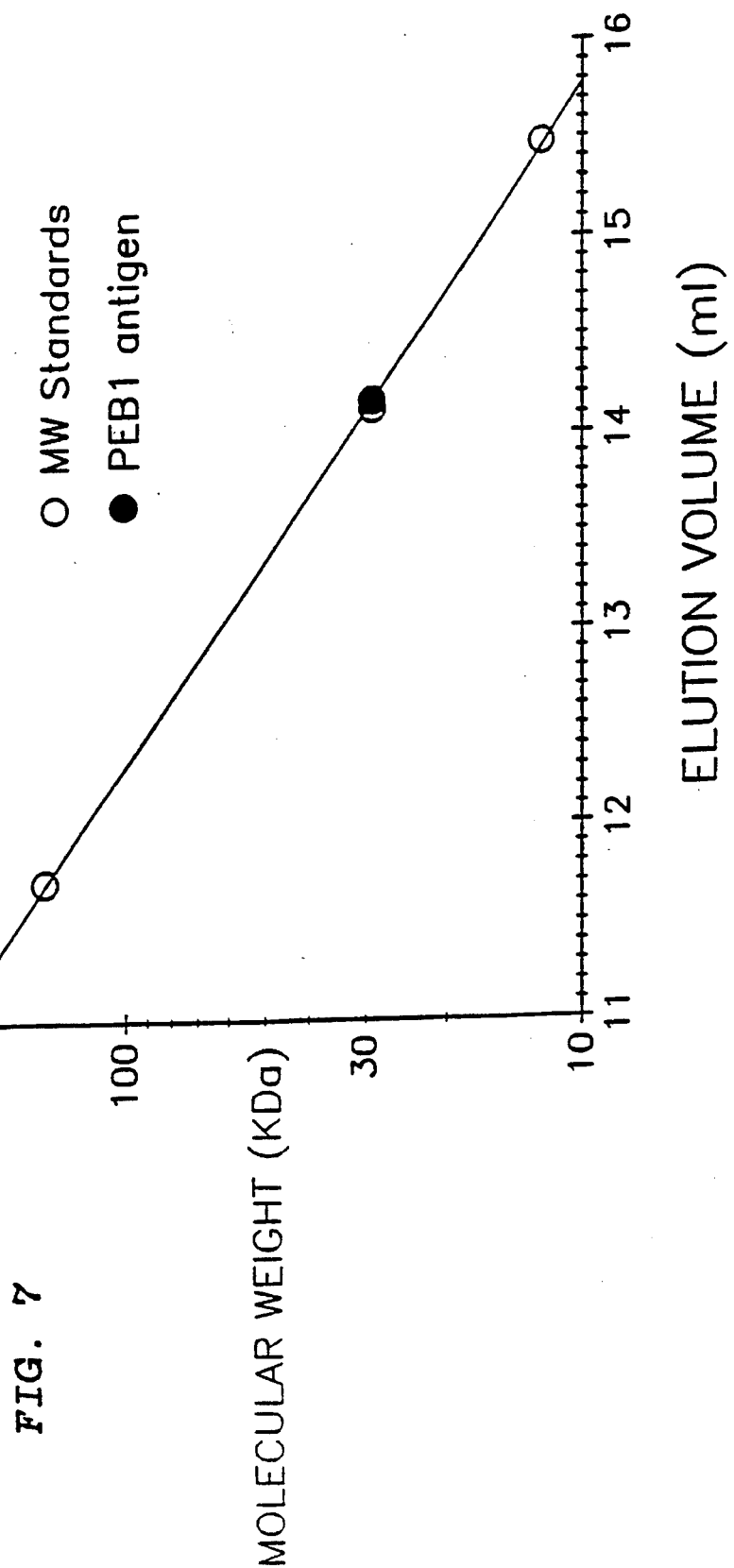
FIG. 7 is a graph of native molecular weight versus elution volume on a Superose 12 column (Pharmacia LKB, Piscataway, N.J.) on a PEB1 antigen from *C. jejuni* and *C. coli*. Gel filtration chromatography results shown in FIG. 7 confirm that the native molecular weight of PEB1 is substantially the same as apparent molecular weight derived from SDS-PAGE analysis. Semilog regression of molecular weights (MW) of five standard proteins ranging from 12.4 to 443 kDa (see text) are used versus their elution volumes (EV), a formula of $\log_{10}[MW]=5.53305-0.28746[EV]$ was generated with a correlation coefficient, r=0.99901.

To further confirm the specificity of recognition of Campylobacter strains in ELISA by antiserum to PEB1 antigen in Example 2, we performed Western blotting to examine for the bands recognized by this serum in preparations of whole bacterial cells of various Campylobacter and Helicobacter species. Whole bacterial cells were prepared as described in Example 2. 0.5 mg of bacterial protein was loaded in each lane in SGS-PAGE with 15% acrylamide. The method of Towbin et al. [Proc. Nat'l. Acad. Sci., 76:4350–54 (1979)] formed the basis of the Western blot procedure we used. In brief, SDS-PAGE was performed with a gel thickness of 0.75 mm in a mini-protean II dual slab cell (Bio-Rad Laboratories, Richmond, Calif.) at 250 mA for about 40 minutes. The proteins were then transferred from the slab gel to nitrocellulose paper by electroblotting for 30 minutes at 1000 mA. The nitrocellulose paper was then blocked once for 30 minutes in Tris/saline blotting buffer (TSBB) (10 mM Tris base, pH 8.0, 0.5M NaCl, 0.5% Tween 20, 0.02% $NaN_3$). The nitrocellulose paper was incubated with a 1:2000 dilution of antiserum to PEB1 from strain 81-176 in TSBB for 60 minutes. After three washes in TSBB, the nitrocellulose paper was incubated with 1:2000 dilution of Alkaline phosphatase-conjugated anti-rabbit IgG (Amersham Corp., Arlington Heights, Ill.) for 60 minutes. After washing, the nitrocellulose paper was developed in substrate solution containing 9 ml of 3 mM $MgCl_2$ in 50 mM tris, pH 10.0, 1 ml of 0.1% nitrobluetetrazolium and 0.1 m. of 0.5% of 5-bromo-4-chloro-3-indoxlyphosphate (Sigma, St. Louis, Mo.) in dimethyl formamide. In total, 18 *C. jejuni* strains, 14 *C. coli*, 3 *C. fetus*, 4 *C. laridis* strains and 1 *H. pylori* strain were tested. A 28 kDa band was found in all 18 *C. jejuni* and all 14 *C. coli* strains, but not found in any of the *C. fetus*, *C. laridis*, or *H. pylori* strains tested (FIG. 3). Thus, this Western blot experiment provided physical evidence that PEB1 antigen from various *C. jejuni/coli* strains are all antigenically related and can be recognized by antiserum to PEB1 antigen from a single strain, 81-176 (ATCC55026). This specificity forms the basis for using PEB1 protein and antibody to this protein in diagnosis of *C. jejuni/coli* infection. In addition to confirming the reliability of ELISA results in EXAMPLE 2, the Western blot shown here is another useful tool in diagnosis.

EXAMPLE 4

Digestion of PEB1 Antigen with Proteinase K

An important question to resolve is whether PEB1 antigen is a protein. To answer this, 24-hour cultures of Campylobacter strains on blood agar plates were harvested in sterile distilled $H_2O$ (5 ml/plate). The cells were pelleted at 3500 g for 10 minutes and resuspended in $H_2O$. The protein concentration was determined using the BCA protein assay kit (Pierce, Rockford, Ill.) and adjusted with $H_2O$ to 240 ug/ml. For enzyme digestion, 2.4 ug of proteinase K (1 ug/ul) was added to 100 ul of bacterial suspension. Proteinase K was replaced by $H_2O$ in control digestions. The mixture was incubated at 37° C. in a water bath for 60 minutes, then 100 ul of SDS-sample buffer was added. The samples were mixed and boiled for 5 minutes, then kept at room temperature to cool, and then run on SDS-PAGE with 15% acrylamide. 8 ul of sample was loaded per lane. Western blot was performed as described in EXAMPLE 3. After electrophoresis, the gel was transferred onto nitrocellulose paper. The nitrocellulose paper was blocked and then reacted with rabbit-anti PEB1. The second antibody was alkaline phosphatase conjugated-goat-anti-rabbit IgG. After washing, the nitrocellulose paper was developed to visualize 28 kDa bands as described in EXAMPLE 3. The 28 kDa band disappeared after proteinase K digestion, but not after the control digestion of all four *C. jejuni/coli* strains and of the glycine extract of *C. jejuni* strain 81-176. This indicates that the major antigenic component of PEB1 antigen is a protein (FIG. 2).

EXAMPLE 5

Determination of Native Molecular Weight of PEB1 Antigen

The native molecular weight of PEB1 antigen was determined in a Superose 12 (Pharmacia LKB, Piscataway, N.J.) gel filtration column using gel filtration molecular weight markers (Sigma, St. Louis, Mo.), assigned as follows: horse spleen apoferritin (443,000), sweet potato beta-amylase (200,000), yeast alcohol dehydrogenase (150,000), bovine erythrocyte carbonic anhydrase (29,000) and horse heart cytochrome C(12,400). Blue dextran (2,000,000) was used to determine the void volume. Individual protein standards were dissolved in a equilibration buffer containing 50 mM tris-HCl, 100 mM KCl, pH7.5. Glycine extracts of *C. jejuni/coli* were dialyzed against water to remove glycine using the Centricon-10 (Amicon, Danvers, Mass.) microconcentrator. First water extracts of *C. jejuni/coli* strains were concentrated in the same way as for the glycine extracts. These samples were diluted 1:1 with the tris-KCl buffer, then either 50 ul of sample or a molecular weight protein standard was loaded into the column. Elution volume of the standards was individually determined by the position of the absorption peak at 280 nm. A standard curve of molecular weight was generated by semilog regression of elution volume versus $Log_{10}$ molecular weight of the protein standard. Elution volume of PEB1 antigen was determined by checking for the presence of the 28 kDa band in each fraction using SDS-PAGE and Western blot with rabbit anti-PEB1 as described in EXAMPLE 3. Two *C. jejuni* (strains 81-176, D1916) and two *C. coli* (strains D743 and D1035) strains were used in this study. In glycine extracts, PEB1 antigen was consistently eluted off the column immediately after the molecular weight standard protein carbonic anhydrase (29 kDa) (FIG. 3), and had a calculated molecular weight of 28.9 kDa, indicating that the PEB1 antigen is a monomer. To compare effect of conditions for extraction on polymerization of PEB1 antigen, we included water extracts in this study. Only trace amounts of PEB1 antigen was extracted in water, so the water extract was concentrated 50-fold by Centriprep-10 (Amicon) concentrator before use. PEB1 antigen extracted in water also was found to be a monomer of 28.9±1.0 kDa for each of four strains tested. In conclusion, the native form of PEB1 antigen was a monomer of 28.9±1.0 kDa, a comparable value to that determined by SDS-PAGE under reducing and denaturing condition (28 kDa). The PEB1 antigens in *C. jejuni* strains have the same native molecular weights as those in *C. coli* strains.

EXAMPLE 6

Preparation of an Oral Vaccine for Administration to Mammals or Poultry

We have considered the potential application of the use of the PEB1 and/or PEB3 antigens in the development of a vaccine against *C. jejuni* and *C. coli* infections. To limit the effects of gastric acid and proteolytic enzymes on the vaccine preparation, the whole PEB1 and/or PEB3 antigen (or a fragment of one or both of these proteins) will be packaged either in an enteric coated gelatin capsule or administered with sodium bicarbonate (Black et all, "Immunogenicity of Ty21a attenuated *Salmonella typhi* given with sodium bicarbonate or in enteric-coated capsules." Dev. Biol. Stand. 53:0, 1983). Dosage for adult humans preferrably varies from 5.0–50.0 mg of the antigens of the invention, which may be either pure PEB1, pure PEB3, or a mixture of PEB1 and PEB3, for example, a dosage of about 10.0 mg of pure or mixed antigen.

To enhance delivery of PEB1 and/or PEB3 to the gastrointestinal immune system the protein(s) [or a fragment(s) of the proteins] may be incorporated without chemical coupling into biodegradable microspheres that are 5–10 μm in size that will be ingested orally (Eldridge et al., "Biodegradable microsphere: vaccine delivery systems for oral immunization," Curr. Top. Microbiol. Immunol. 146:59, 1989). The microspheres are composed of co-polymers of glycolic and lactic acids which are degraded into original components by hydrolysis. Adjusting the ratio of glycolic to lactic acids within the co-polymers varies the rate of hydrolysis from several hours to several months. Thus, both fast- and slow-releasing microspheres can be created. The use of a mixture of both fast- and slow-releasing microspheres will then be used to allow for induction of both a primary and secondary immune response with a single oral immunization.

EXAMPLE 7

Preparation of a Parenteral Vaccine for Administration to Mammals or Poultry

Although for gastrointestinal pathogens, orally administered vaccines appear to be preferable, for several other infectious agents, parenteral vaccine show efficacy. A component of the bacterium *Salmonella typhi,* the cause of typhoid fever, has been purified and used as a parenteral-administered vaccine. This component, the Vi capsular polysaccharide, is highly efficacious (Klugman K. P., et al. Protective activity of Vi capsular polysaccharide vaccine against typhoid fever, "Lancet 1987;2:1165–69"). The Salk vaccine for polio is administered parenterally and it prevents the disease of polio, although having little or no effect on becoming infected with the polioviruses. Parenteral vaccines also have efficacy, although limited, in preventing cholera.

For *C. jejuni,* a parenteral vaccine could include PEB1 and/or PEB3 or fragments thereof. The protein(s) or fragment(s) could be administered with an adjuvant or by itself in a suitable buffer. Reasonable adjuvants include, but are not limited to, muramyl dipeptide, concanavalin A, DEAE dextran, lipid polyvalent cations, or hydrocarbons such as hexadecane.

*C. jejuni* vaccine could be given to humans as 1.0 mg (range 0.5–5.0 mg) of antigen (PEB1, PEB3, or mixture of both) in 1 ml of phosphate buffered saline (pH7.4). With a suitable antigen, only a single dose may be needed, but multiple doses with or without adjuvants could be considered.

EXAMPLE 8

*C. jejuni/C. coli*-specific test kits are constructed for detecting antibodies using several different techniques for detection. One test kit for antibody detection comprised of a compartmented enclosure containing a plurality of wells, plates which were coated prior to use with PEB1 or PEB3 antigens, and ELISA materials for enzyme detection consisting of peroxidase-labeled goat anti-human IgG and a color change indicator consisting of ABTS in McIlvain's buffer with 0.005 percent hydrogen peroxide. Naturally, other enzymes and developers could have been used. For instance, alkaline phosphatase-labelled goat anti-human IgG could be used in conjunction with p-nitrophenyl phosphate in diethanolamine and magnesium chloride buffer.

A second test kit for detecting antibodies using the Western blot technique is comprised of a container, cover, nitrocellulose sheet, and a polyacrylamide slab gel in the presence of sodium dodecyl sulfate, surfactants, pH modifiers, dried non-fat milk and materials for enzyme detection including a color change indicator consisting of DAB in Tris with hydrogen peroxide. This Western blot analysis kit also contains peroxidase-labelled goat or rabbit anti-human immunoglobulin and a source of PEB1 or PEB3 antigens.

Another *C. jejuni/C. coli*-specific test kit for detecting antibodies using the indirect immunofluorescence assay may include a compartmental container with PEB1 or PEB3 antigens, human test serum, phosphate buffered saline and fluorescein-conjugated goat anti-human IgG.

Finally, a different *C. jejuni/C. coli* specific test kit for detecting antibodies uses liposomes and comprises a container, human test serum, fluorescent marker- (or enzyme- or substrate-) filled liposome with *C. pylori* antigens on their surface, and a surface-active agent. In this assay the container mght be a precoated tube or well with goat anti-human IgG.

*C. jejuni/C. coli*-specific test kits are constructed for detecting *C. jejuni* or *C. coli* cells using several different techniques for detection. One test kit for detection of *C. jejuni* or *C. coli* cells comprises a compartmented enclosure containing a plurality of wells, plates that could be coated with cells of the bacterial strain to be tested, a hyperimmune antiserum to PEB1 antigen, and appropriate ELISA materials such as those discussed above in this example.

A second test kit for detecting *C. jejuni* or *C. coli* cells using the Western blot technique is comprised of a container, cover, nitrocellulose sheet, and a polyacrylamide slab gel in the presence of sodium dodecyl sulfate, surfactants, pH modifiers, dried non-fat milk and materials for enzyme detection including a color change indicator consisting of DAB in Tris with hydrogen peroxide. This Western blot analysis kit also contains goat anti-rabbit immunoglobulin and a source of hyperimmune antiserum to PEB1.

Another *C. jejuni/C. coli*-specific test kit for detecting antibodies using the latex agglutination assay may include a compartmental container, hyperimmune serum to PEB1 and/or PEB3 conjugated to latex beads, and phosphate buffered saline or water.

The kits described above could be utilized for detection of *C. jejuni* or *C. coli* organisms in fecal or water specimens, fecal or water specimens enriched for Campylobacter by selective enrichment methods, or in colonies on solid media suspected as being *C. jejuni* or *C. coli.*

The terms and descriptions used herein are preferred embodiments set forth by way of illustration only, and are not intended as limitations on the many variations which those of skill in the art will recognize to be possible in practicing the present invention as defined by the patent claims based on the present disclosure.

What is claimed is:

1. Antisera raised against a purified PEB1 antigen which is obtained from *Campylobacter jejuni* and has an apparent molecular weight of 28 kDa as measured on sodium dodecyl sulfate polyacrylamide gel under reducing conditions, a molecular weight of 28.9±1.0 kDa as measured by gel filtration chromatography under native conditions, and an isoelectric point of 8.5.

* * * * *